United States Patent
Chan et al.

(10) Patent No.: US 8,844,725 B2
(45) Date of Patent: Sep. 30, 2014

(54) TEST STRIP CONTAINER WITH STRIP RETAINER AND METHODS OF MANUFACTURING AND UTILIZATION THEREOF

(75) Inventors: Frank A. Chan, Sunnyvale, CA (US); Matthew C. Sauers, Indianapolis, IN (US); Abner D. Joseph, Carmel, IN (US); Christopher Wiegel, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 823 days.

(21) Appl. No.: 12/690,152

(22) Filed: Jan. 20, 2010

(65) Prior Publication Data

US 2011/0174644 A1  Jul. 21, 2011

(51) Int. Cl.
*B65D 85/30*    (2006.01)
*B65D 43/16*    (2006.01)
*B65D 25/10*    (2006.01)
*A61B 19/02*    (2006.01)
*A61B 10/00*    (2006.01)

(52) U.S. Cl.
CPC .............. *B65D 43/16* (2013.01); *B65D 25/102* (2013.01); *A61B 19/026* (2013.01); *A61B 2010/0006* (2013.01); *Y10S 206/805* (2013.01)
USPC ............ 206/569; 206/305; 206/486; 206/805

(58) Field of Classification Search
USPC ........... 206/305, 569, 486, 488, 805; 422/401
See application file for complete search history.

(56) References Cited

U.S. PATENT DOCUMENTS

| | | | | |
|---|---|---|---|---|
| 3,159,272 A | * | 12/1964 | Swift | 206/246 |
| 4,793,478 A | * | 12/1988 | Tudor | 206/256 |
| 5,810,164 A | * | 9/1998 | Rennecamp | 206/256 |
| 5,976,895 A | * | 11/1999 | Cipkowski | 436/518 |
| 6,193,873 B1 | | 2/2001 | Ohara et al. | |
| 6,475,372 B1 | | 11/2002 | Ohara et al. | |
| 6,558,528 B1 | | 5/2003 | Matzinger | |
| 6,620,310 B1 | | 9/2003 | Ohara et al. | |
| 6,716,577 B1 | | 4/2004 | Yu et al. | |
| 7,059,492 B2 | * | 6/2006 | Giraud et al. | 220/834 |
| 7,172,728 B2 | | 2/2007 | Otake | |
| 2003/0186446 A1 | * | 10/2003 | Pugh | 436/46 |
| 2004/0007585 A1 | | 1/2004 | Griffith et al. | |
| 2007/0080093 A1 | | 4/2007 | Boozer et al. | |
| 2007/0196240 A1 | | 8/2007 | Boozer et al. | |
| 2009/0143701 A1 | * | 6/2009 | Ghesquiere et al. | 600/583 |

(Continued)

FOREIGN PATENT DOCUMENTS

| | | |
|---|---|---|
| EP | 0 779 226 A1 | 12/1996 |
| EP | 2 031 389 A1 | 9/2007 |
| GB | 2 443 893 A | 5/2008 |

OTHER PUBLICATIONS

International Search Report, Application No. PCT/EP2011/050657, Apr. 15, 2011, 10 pgs.

*Primary Examiner* — Jacob K Ackun
(74) *Attorney, Agent, or Firm* — Dinsmore & Shohl LLP

(57) ABSTRACT

A test strip container with an insert comprising a channel and a retaining member and methods of manufacturing and utilization thereof are disclosed. The container includes a housing, an insert, a lid, and at least one retaining member in at least one channel. The at least one retaining member releasably retains a plurality of test strips in the at least one channel.

15 Claims, 15 Drawing Sheets

(56) References Cited

U.S. PATENT DOCUMENTS

2009/0321467 A1* 12/2009 West et al. .................... 221/1
2010/0000905 A1* 1/2010 Wang et al. .................... 206/569
2011/0056951 A1* 3/2011 Wooldridge ............. 220/495.01
2011/0127175 A1* 6/2011 Chan et al. .................... 206/204

* cited by examiner

TEST STRIP CONTAINER WITH STRIP RETAINER AND METHODS OF MANUFACTURING AND UTILIZATION THEREOF

TECHNICAL FIELD

Embodiments of the disclosure relate generally to containers for test strips, and especially to a test strip container with expandable insert, and methods of manufacturing and utilization thereof.

BACKGROUND

Apparatuses and methods for testing compositions of biological fluids, as well as test strips for use in such devices, are well known. Typically, test strips are stored in a separate disposable vial, distinct from the test apparatus that analyzes the fluid sample. A test strip is first removed from the vial container, a sample of biological fluid is deposited onto the strip, and the strip is inserted into a test strip meter for analysis of the desired component. After the analysis is complete, the test strip is ejected from the meter and disposed.

The problem with storing the test strips in the disposable vials is the difficulty in dispensing a single strip to a user, while maintaining the small, compact profile of the vial. Often the individuals who perform blood glucose testing have difficulty handling the vials, and retrieving only a single test strip. Typically, a user will invert the vial to dispense a strip. Then, several strips will pour out of the container, rather than just the desired quantity. The user must then isolate a single strip and replace the other unused strips before they are contaminated by environmental forces.

Test strips may also be packaged individually in tear-away blister packages. In order for a person to use a single test strip, the blister package must be ripped opened and the test strip must then be removed. Both of these steps may be difficult for one with impaired circulation. Furthermore, carrying enough blister packs for a proper testing routine may be inconvenient and cumbersome.

SUMMARY

It is against the above background that embodiments of the present disclosure provide a test strip container with a retaining member and methods of manufacturing and utilization thereof. Generally, the test strip container provides test strips to a user in an easily accessible fashion, without accidental dumping or spilling.

In one embodiment, a container for storing a plurality of test strips comprises a housing. The housing has a front housing portion opposing a rear housing portion. The front housing portion has a height H1 and the rear housing portion has a height H2. The housing defines a cavity having a base. A lid is hingedly connected to the rear housing portion and has a front lid portion opposing a rear lid portion. The front lid portion has a height H3 and the rear lid portion has a height H4. An insert is provided in the cavity of the housing and has at least one channel with at least one retaining member provided lengthwise which releasably retains the plurality of test strips substantially perpendicular to the base of the housing.

In another embodiment, a container for storing a plurality of test strips comprises a housing. The housing has a front housing portion opposing a rear housing portion. The front housing portion has a height H1 and the rear housing portion has a height H2. The housing defines a cavity having a base. A lid is hingedly connected to the rear housing portion and has a front lid portion opposing a rear lid portion. The front lid portion has a height H3 and the rear lid portion has a height H4. An insert is provided in the cavity of the housing and has at least one channel with at least one retaining member provided lengthwise which releasably retains the plurality of test strips substantially perpendicular to the base of the housing. The retaining member further comprises a biasing member connected adjacent to the front housing portion and which presses against and compressibly retains the plurality of test strips towards the front of the cavity.

In yet another embodiment, a container for storing a plurality of test strips comprises a housing defining a cavity having a base. The housing has a front grip, a rear grip, and a front housing portion opposing a rear housing portion. The front housing portion has a height H1 and the rear housing portion has a height H2, wherein H1≤H2. The height difference between heights H1 and H2 defines an angle α which ranges from 0 to 14 degrees. A lid is hingedly connected to the rear housing portion. The lid has a front lid portion opposing a rear lid portion. The front lid portion has a height H3 and the rear lid portion has a height H4, wherein H3≥H4 and the height difference between heights H3 and H4 defines an angle β which ranges from 0 to 14 degrees. An insert is provided in the cavity of the housing and has an insert surface angled at γ relative the base of the housing. At least one channel having at least one retaining member is provided lengthwise along the channel which releasably retains the plurality of test strips substantially perpendicular to a housing base.

In another embodiment, a method of manufacturing a container for storing a plurality of test strips comprises providing a housing with a cavity and a lid hingedly connected to the housing for closing the cavity. An insert is introduced within the cavity. The insert comprises a channel defined by two longitudinal sides. At least one retaining member is provided lengthwise along the longitudinal sides of the channel.

These and other features and advantageous of these and other various embodiments according to the present disclosure will become more apparent in view the drawings, detailed description, and claims provided that follow hereafter.

BRIEF DESCRIPTION OF THE DRAWINGS

The following detailed description of the embodiments of the present disclosure can be best understood when read in conjunction with the following drawings, where like structure is indicated with like reference numerals, and in which.

Skilled artisans appreciate that elements in the figures are illustrated for simplicity and clarity and have not necessarily been drawn to scale. For example, the dimensions of some of the elements in the figures may be exaggerated relative to other elements, as well as conventional parts removed, to help to improve understanding of the various embodiments of the present disclosure.

DETAILED DESCRIPTION

Figure 1A:
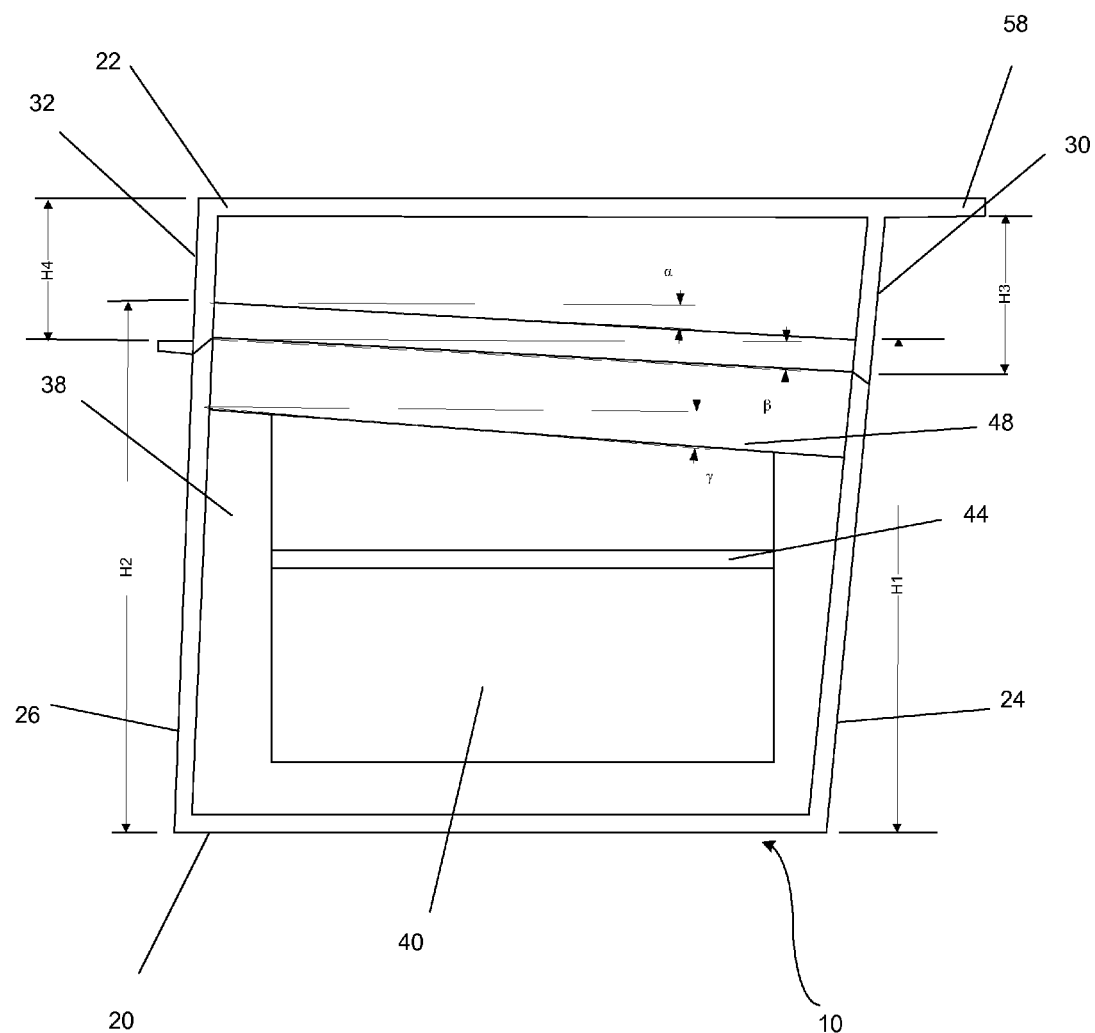
FIGS. 1A and 1B show cross-sectional side views of a test strip container in accordance with one embodiment.
Figure 1B:
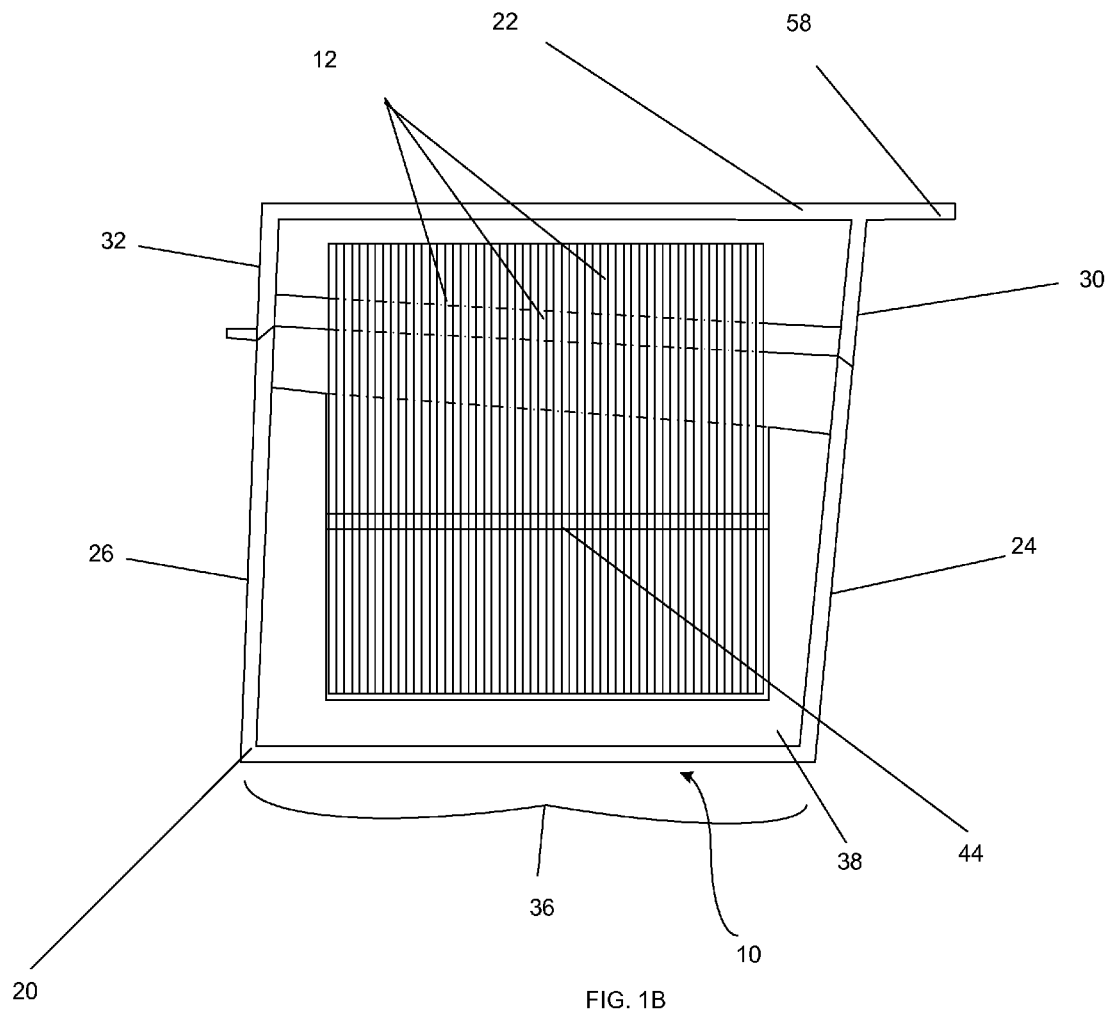

With reference to FIGS. 1A and 1B, in one embodiment, a test strip container 10 is disclosed for storing and dispensing test strips 12, and particularly for easily dispensing a single test strip 12 from a plurality of test strips 12, i.e., dispensing one test strip 12 at a time. Additionally, the test strip container 10 protects test strips 12 from adverse contaminants and conditions such as air, light, humidity, dust, dirt, oils, or other contaminants. The test strip container 10 also allows for easy re-loading of additional test strips 12, as will be apparent from the descriptions below.

Figure 2:
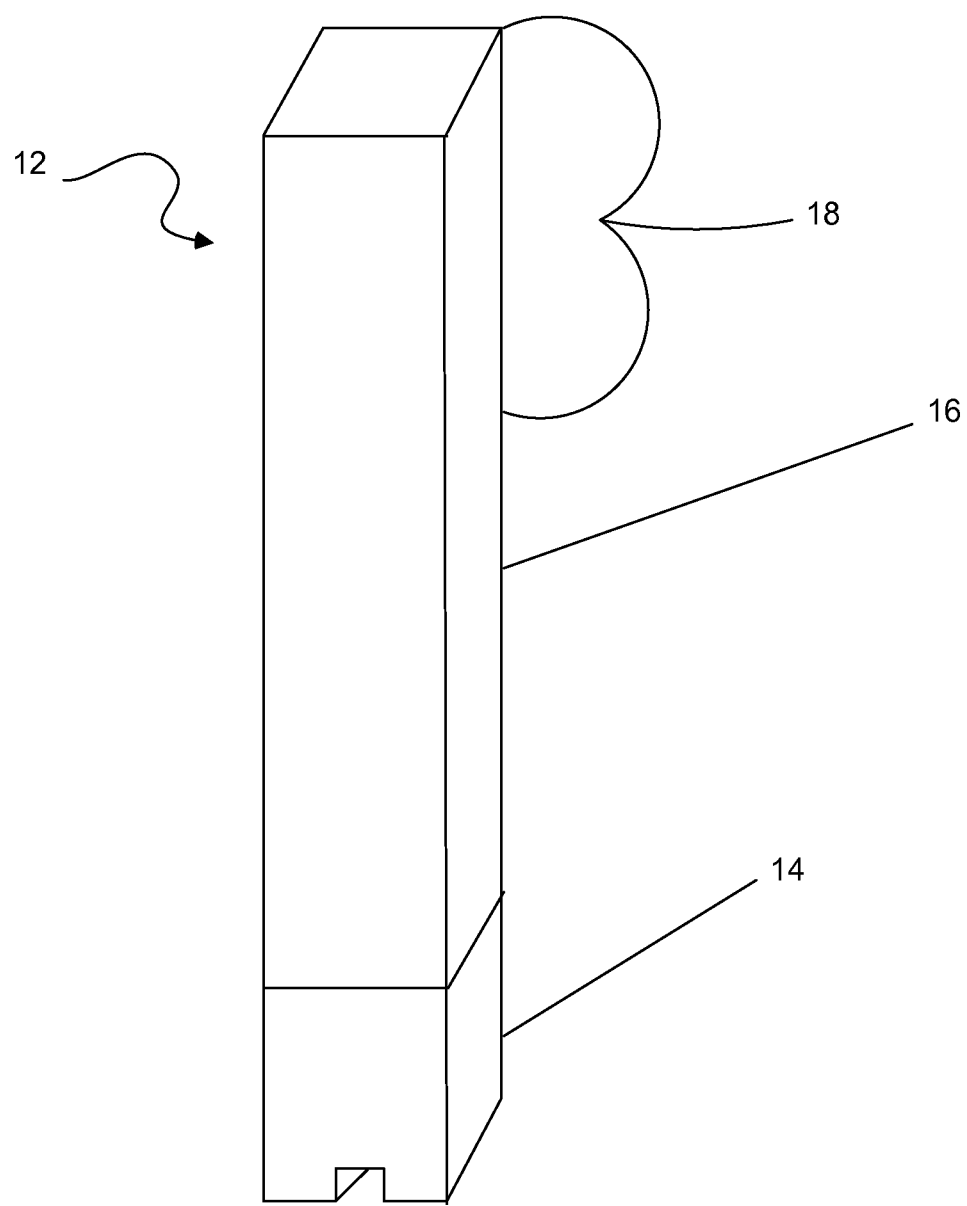
FIG. 2 shows a front perspective view of a test strip container in accordance with one embodiment.

In further describing the embodiments of the present disclosure, a conventional test strip 12 is described with reference made to FIG. 2 by way of example and not limitation. The illustrated test strip 12 shown by FIG. 2 is generally made up of at least the following components: a reagent portion 14 for receiving a sample and a support element 16 providing a handling portion 18. A test strip meter may be used to analyze the test strip 12 to automatically determine an analyte concentration in the sample provided to the reagent portion 14.

As shown, the reagent portion 14 is attached to the support element 16, in which the support element may be of a material (or material layers) that is sufficiently rigid to be inserted into a test strip meter without undue bending or kinking. In one embodiment, the support element 16 can be made of material(s) such as polyolefins, e.g., polyethylene or polypropylene, polystyrene or polyesters, and combinations thereof where in embodiments having a support element 16 formed from layers, such materials may be the same or different. Consequently, the length of the support element 16 typically dictates or corresponds to the length of the test strip 12.

Regardless of whether or not the length of the support elements 16 dictates or corresponds to the length of the test strip 12, the length of the test strip 12 generally ranges from about 3 mm to about 1000 mm, usually from about 10 mm to about 100 mm, and more usually from about 20 mm to about 60 mm.

As described above, the support element 16 is usually configured to enable the test strip 12 to be inserted into a test strip meter. As such, the support element 16, and thus the test strip 12, are typically in the form of a substantially rectangular or square-like strip, where the dimensions of the support element 16 vary according to a variety of factors, as will be apparent to those of skill in the art, and may be the same or different.

Examples of such test strips suitable for use with the subject disclosure include those described in copending U.S. application Ser. Nos. 09/333,793; 09/497,304; 09/497,269; 09/736,788 and 09/746,116, the disclosures of which are herein incorporated by reference.

With reference to FIGS. 1A-B, in one embodiment, the housing 20 and lid 22 may be formed of one integrated assembly. However, the test strip container 10 may be made up of two separate assemblies: a lid 22 and a housing 20. In other words, the lid 22 and the housing 20 are not attached together. Either configuration advantageously enables substantially air and moisture tight seals to be created and maintained between the lid 22 and the housing 20.

The test strip container 10 has a housing 20 and lid 22 each comprising a rigid material that will retain its shape and form without cracking or breaking. The housing 20 and lid 22 may be manufactured from a variety of materials, where the housing 20 and lid 22 may be manufactured from the same or different materials, but where such materials will not interfere with the reagent portion 14 of the test strip 12 retained therein (FIG. 2). Examples of such materials include, but are not limited to, plastics such as polytetrafluoroethylene, polypropylene, polyethylene, polystyrene, polycarbonate, and blends thereof. Materials may also include metals such as stainless steel, aluminum and alloys thereof, siliceous materials and the like.

The housing 20 comprises a front housing portion 24 and a rear housing portion 26. The front housing portion 24 extends from the bottom of the container 10 to the top of the housing 20. The front housing portion 24 opposes a rear housing portion 26, where the front housing portion 24 and rear housing portion 26 are substantially parallel to one another. The rear housing portion 26 extends from the bottom of the container 10 to the top of the housing 20.

Referring again to FIGS. 1A-B, the lid 22 is hingedly connected to the rear housing portion 26 of the housing 20. The housing 20 and lid 22 are alignable in a close configuration, such that the housing 20 and lid 22 form a substantially air and moisture tight seal when in a closed configuration. By substantially air and moisture tight seal, it is meant that the housing 20 and lid 22 are capable of preventing substantial air and moisture from entering the housing 20 when the housing 20 and lid 22 are in a closed configuration.

Figure 3A:
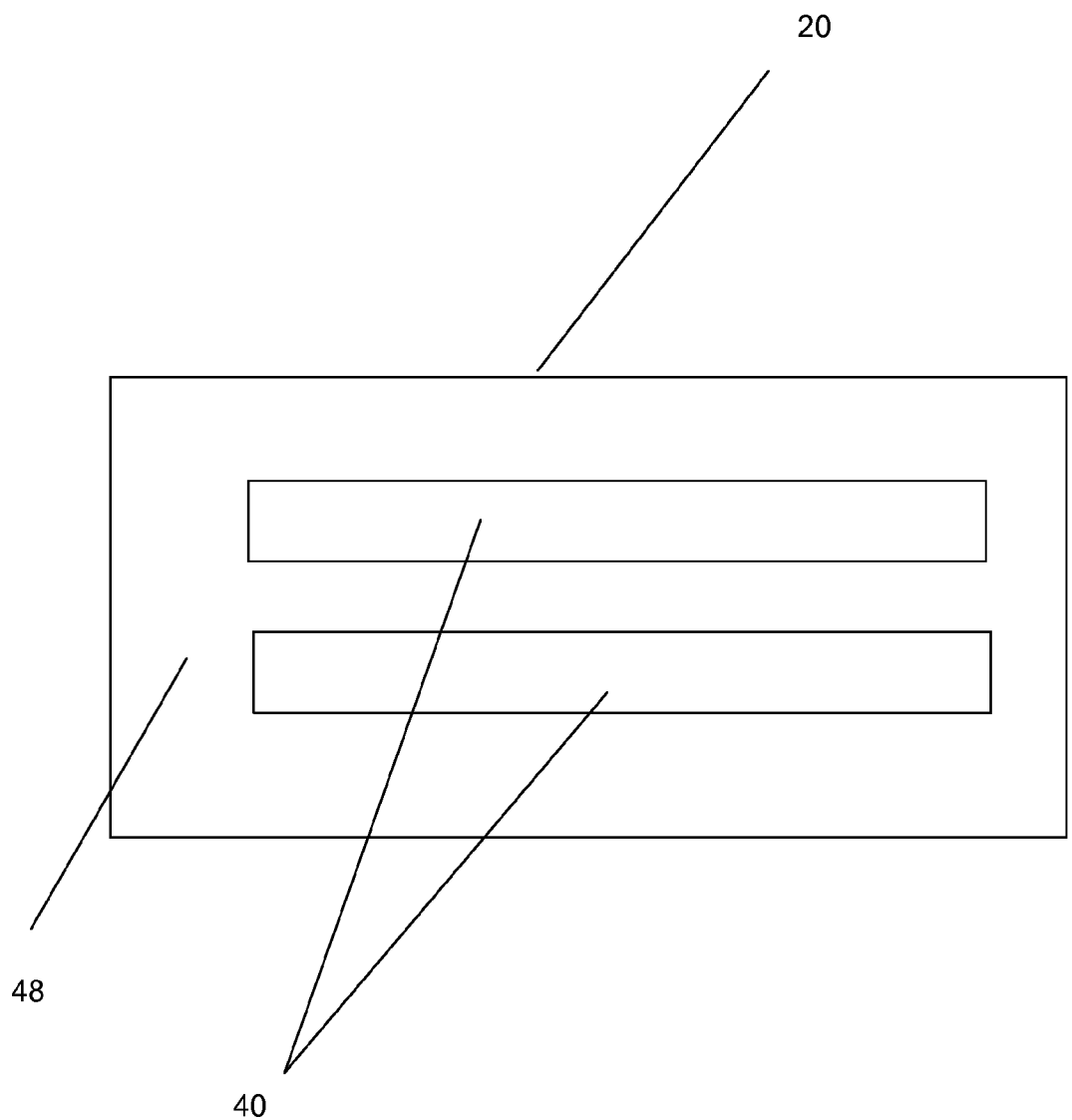
FIGS. 3A and 3B show a top view of a test strip container in accordance with one embodiment.
Figure 3B:
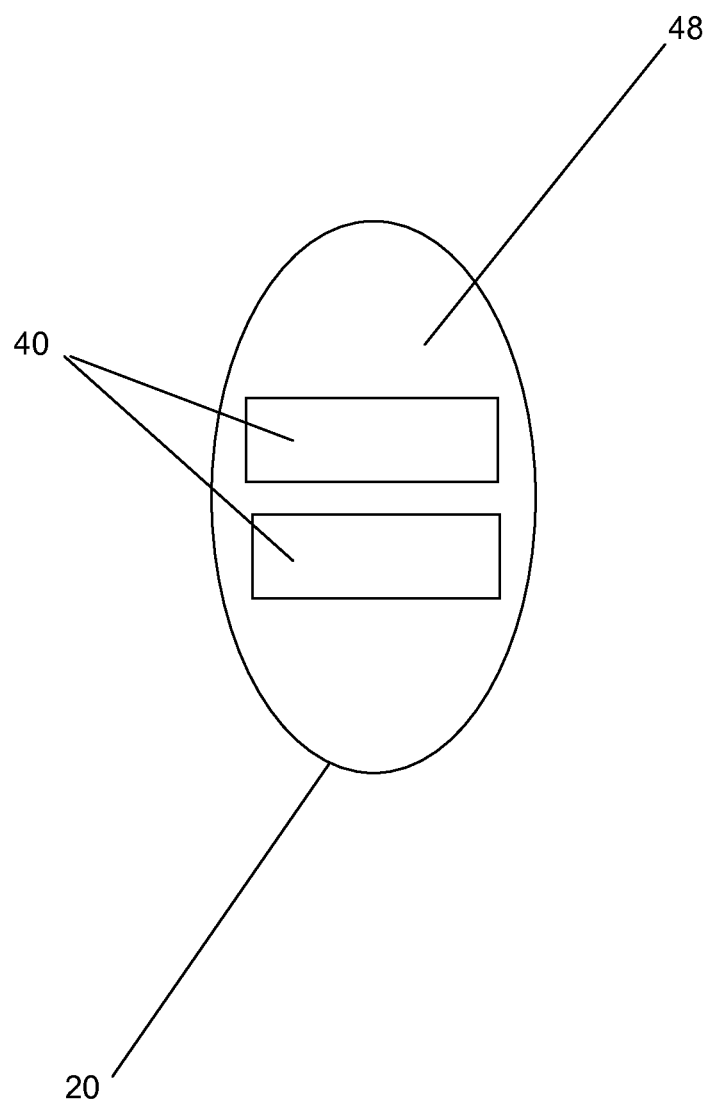

Referring to FIGS. 3A-B, the size and shape of the housing 20 and lid 22 will vary depending on a variety of factors, where such factors include, but are not limited to the type and number of test strips 12 (FIG. 2) retained therein, and the like. Accordingly, the shape of the housing 20 may take any of a variety of shapes. For example, the housing 20 and lid 22 may be substantially rectangular, substantially square, substantially cylindrical, substantially round, substantially circular, substantially elliptical or substantially oval shape. Alternatively, the shape may be more complex such as a substantially irregular shape or the like. The corners and edges of the housing 20 are typically rounded or beveled to avoid any snagging or injury by the user.

Figure 4:
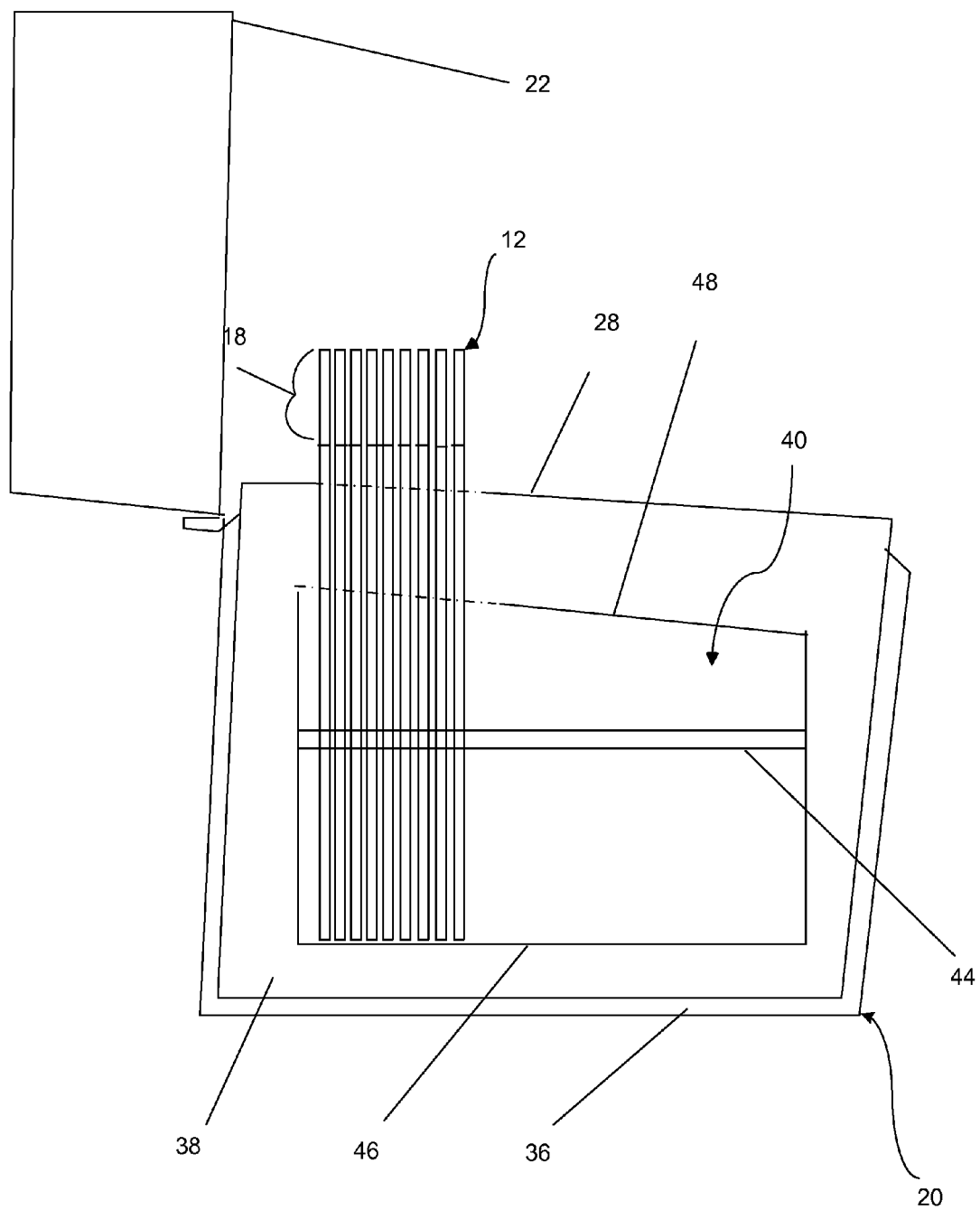
FIG. 4 shows a cross-sectional side view of a test strip container in accordance with one embodiment.

With reference to FIG. 4, the size of the housing 20 may also vary depending on a variety of factors such as the type and number of test strips 12 retained therein. In the illustrated embodiment, the housing 20 and lid 22 are sized and arranged such that at least a fraction of the handling portion 18 of each test strips 12 retained in the container 10 extends beyond the housing distal edge 28 to allow a user to easily grasp it.

Referring again to FIG. 1A, in one embodiment, the housing 20 has a front housing portion 24 opposing a rear housing portion 26. The front housing portion 24 has a height H1. The height H1 may range from about 2 to about 8 cm, however, H1 may more usually range between about 2 to about 4 cm. The rear housing portion 26 has a height H2. The height H2 may range from about 2 to about 10 cm, however, it more usually between about 2 to about 5 cm.

In one embodiment, the height H1 is typically about three-quarters the length of each test strip 12 (i.e., about one-quarter of each test strip 12 protrudes above the housing distal edge 28), but the height H1 may be as little as one half or less the length of each test strip 12 (FIG. 4).

Further referring to FIG. 1A, the lid 22 has a front lid portion 30 opposing a rear lid portion 32. The front lid portion 30 has a height H3. The height H3 may range from about 5-50 mm, however the height H3 may typically be about 5 to about 20 mm. The rear lid portion 32 has a height H4. The height H4 may range from about 5 to about 50 mm, however, the height H4 may more usually range from about 5 to about 20 mm.

In another embodiment, the insert 38 comprises at least one channel 40. In one embodiment, the channel 40 is centered on the face of the insert 38. In another embodiment, the channel 40 may be located off of center of the insert 38. The channel 40 may be oriented lengthwise along the longitudinal side of the insert 38. However, the channel 40 may also be oriented widthwise along the latitudinal side of the insert 38 (FIG. 3B).

Figure 5:
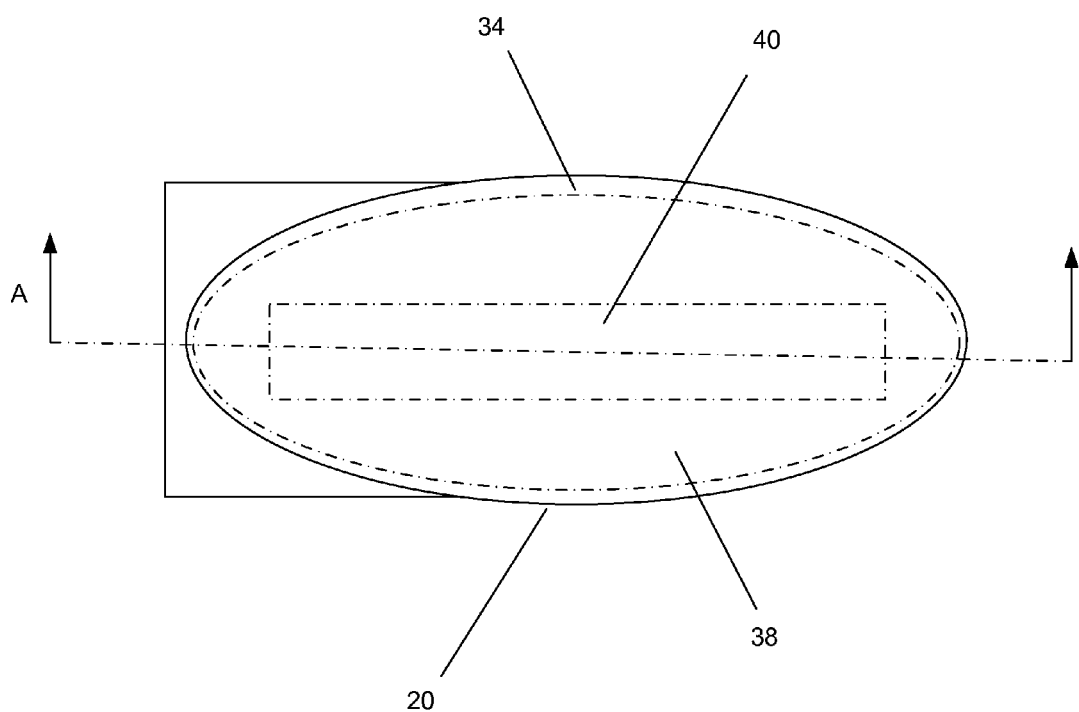
FIG. 5 shows a top view of a test strip container in accordance with one embodiment.

With reference to FIG. 5, in one embodiment, the housing 20 defines a cavity 34 within its inner walls. The cavity 34 extends from the housing base 36 to the housing distal edge 28 (FIG. 1B). An insert 38 may be provided within the cavity 34. The insert 38 may comprise a wide range of materials including a molded desiccant, resin, or polymeric material. The insert 38 may comprise a solid component, or a frame-like mold structure. In one embodiment, the insert 38 may be co-molded onto an inside surface of the cavity 34, or molded as individual part, for later insertion into the cavity 34. In one embodiment, the insert 38 is removably retained within the cavity 34 by friction, interlocking snaps, or a locking mechanism.

Figure 12:
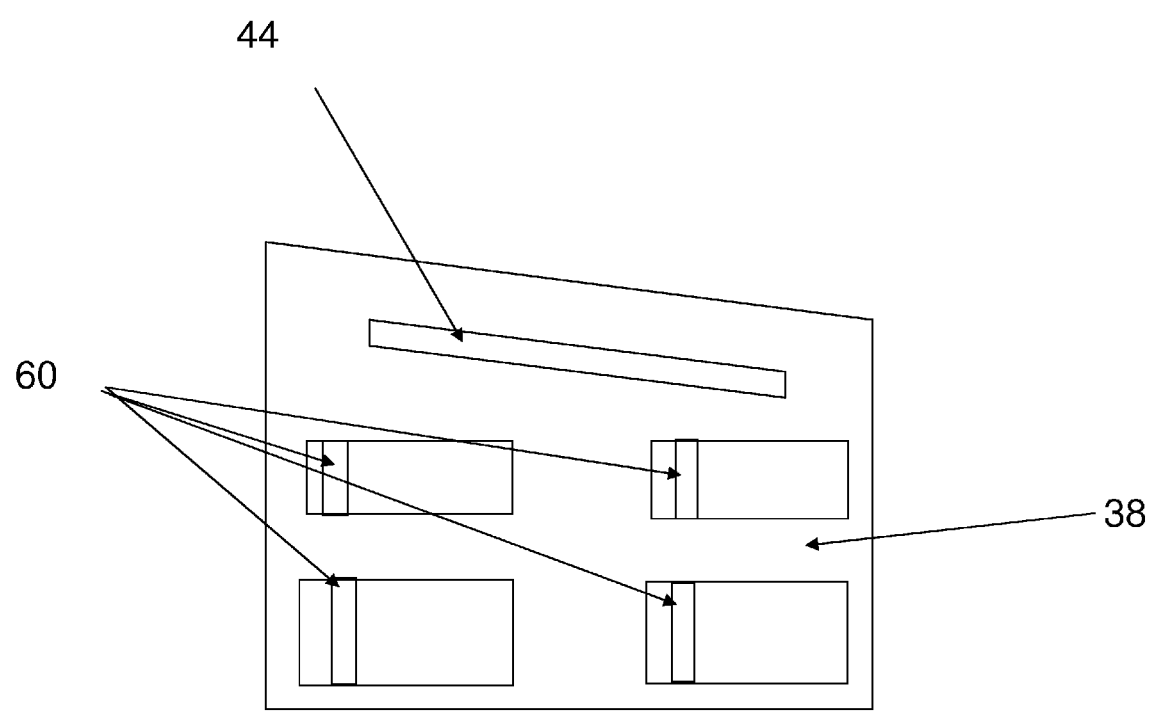
FIG. 12 shows a side view of an insert in accordance with one embodiment.

Referring to FIG. 12, in another embodiment, the insert 38 may comprise at least one structural rib 60 located along the longitudinal sides of the insert 38. Preferably, the insert comprises at least two structural ribs 60 mounted on each of the two longitudinal sides of the insert 38. Alternatively, the insert 38 may comprise several structural ribs 60, for example, four structural ribs 60. The structural ribs 60 are preferably mounted below the retaining member 44. However, other mounting arrangements are contemplated. The structural ribs 60 may operate to support the longitudinal sides of the housing 20, and prevent any potential movement. Preferably, the structural ribs 60 may support the sides of the housing 20 to prevent dislodging the seal between the housing 20 and lid 22.

In addition, the structural ribs may 60 serve as locking mechanism to removably attach the insert 38 to the cavity 34. Preferable, the structural ribs 60 frictionally interact with the cavity 34 below the retaining member 44. However, other forms of locking the insert 38 within the cavity 34 are also contemplated using the structural ribs 60.

With further reference to FIG. 4, in accordance with one embodiment, the channel 40 comprises a rectangular inset with a depth ranging from about 5 to about 50 mm. In another embodiment, the channel 40 has a depth more usually ranging from about 5 to about 20 mm. However, the channel 40 may have a depth sufficient to allow protrusion of the handling portion 18 from the housing distal edge 28 to allow a user to easily remove a test strip 12 from the container 10.

Referring again to FIG. 5, the size of the insert 38 may vary depending on the size of the housing 20, and the test strips 12, and the channel 40. In one embodiment, the insert 38 completely fills the channel 40. In another embodiment, the insert 38 only partially fills the channel 40. The shape of the insert 38 generally corresponds to the shape of the cavity 34, but may take other shapes as well.

Figure 6:
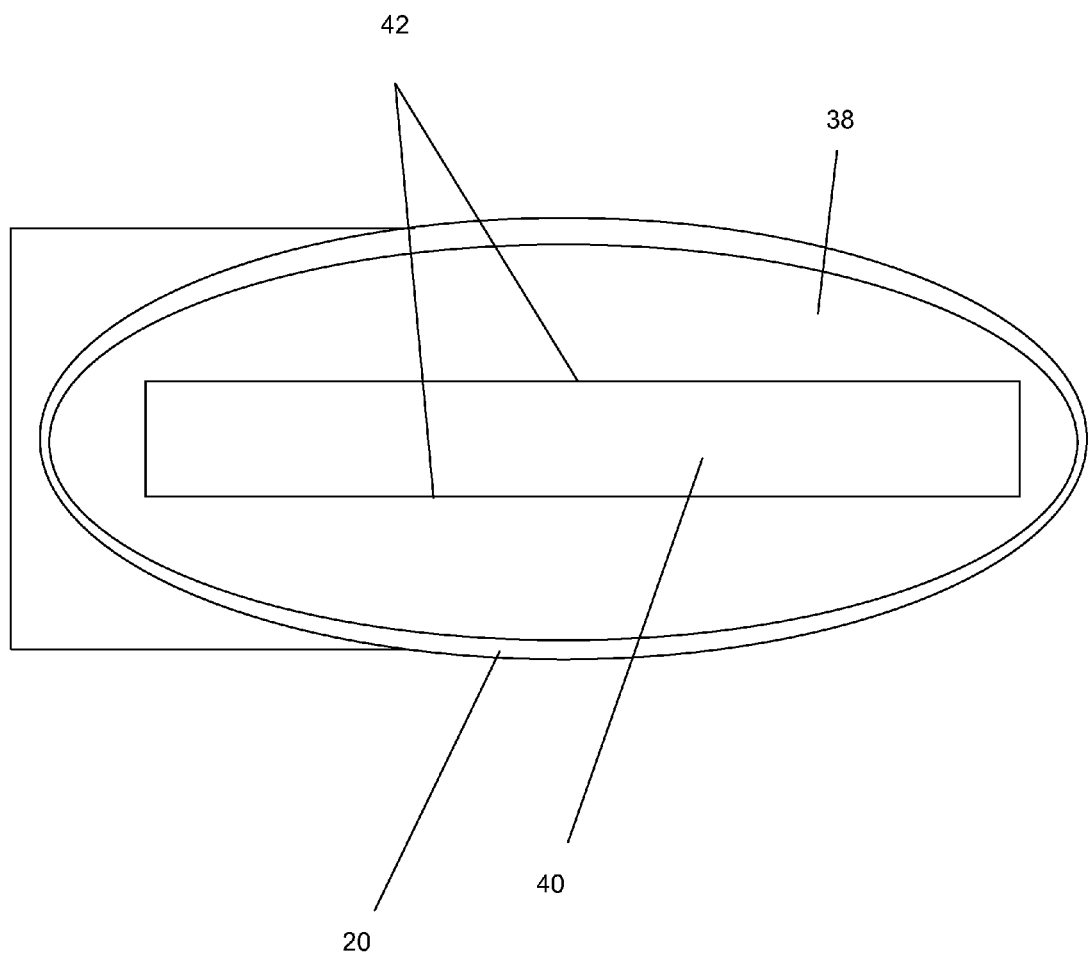
FIG. 6 shows a top view of a test strip container in accordance with one embodiment.

Referring to FIG. 6, a channel 40 may be sized to accommodate at least one test strip 12 (FIG. 2) inserted within the channel 40. In one embodiment, the channel 40 is wider than a test strip 12. In another embodiment, the width of the channel 40 ranges from about 1 to about 10 mm. In another embodiment, the width of the channel 40 ranges from about 2 to about 7 mm.

With further reference to FIG. 6, another embodiment, the length of the channel 40 is long enough to accommodate approximately 1 to approximately 50 test strips 12 arranged in a stack. However, in another embodiment, the length of the channel 40 is long enough to accommodate from approximately 1 to approximately 25 test strips 12. In one embodiment, the length of the channel 40 ranges from about 10 to about 100 mm. In another embodiment, the length of the channel 40 ranges from about 10 to about 50 mm. In yet another embodiment, the length of the channel 40 ranges from about 10 to about 30 mm.

With reference to FIGS. 3A-B, in yet another embodiment, an insert 38 may comprise more than one channel 40. In another embodiment, the insert 38 may comprise 1 to 10 channels 40. The channels 40 may oriented in many different fashions with respect to one another, including substantially parallel, and substantially perpendicular orientations.

In yet another embodiment, where the at least one channel 40 comprises two longitudinal sides 42 which define the length of the channel 40. The longitudinal sides 42 are spaced apart from one another to allow the insertion of a test strip 12 (FIG. 2) oriented perpendicular to the longitudinal sides 42. In one embodiment, the longitudinal sides 42 comprise contracting elastic bands.

Figure 7:
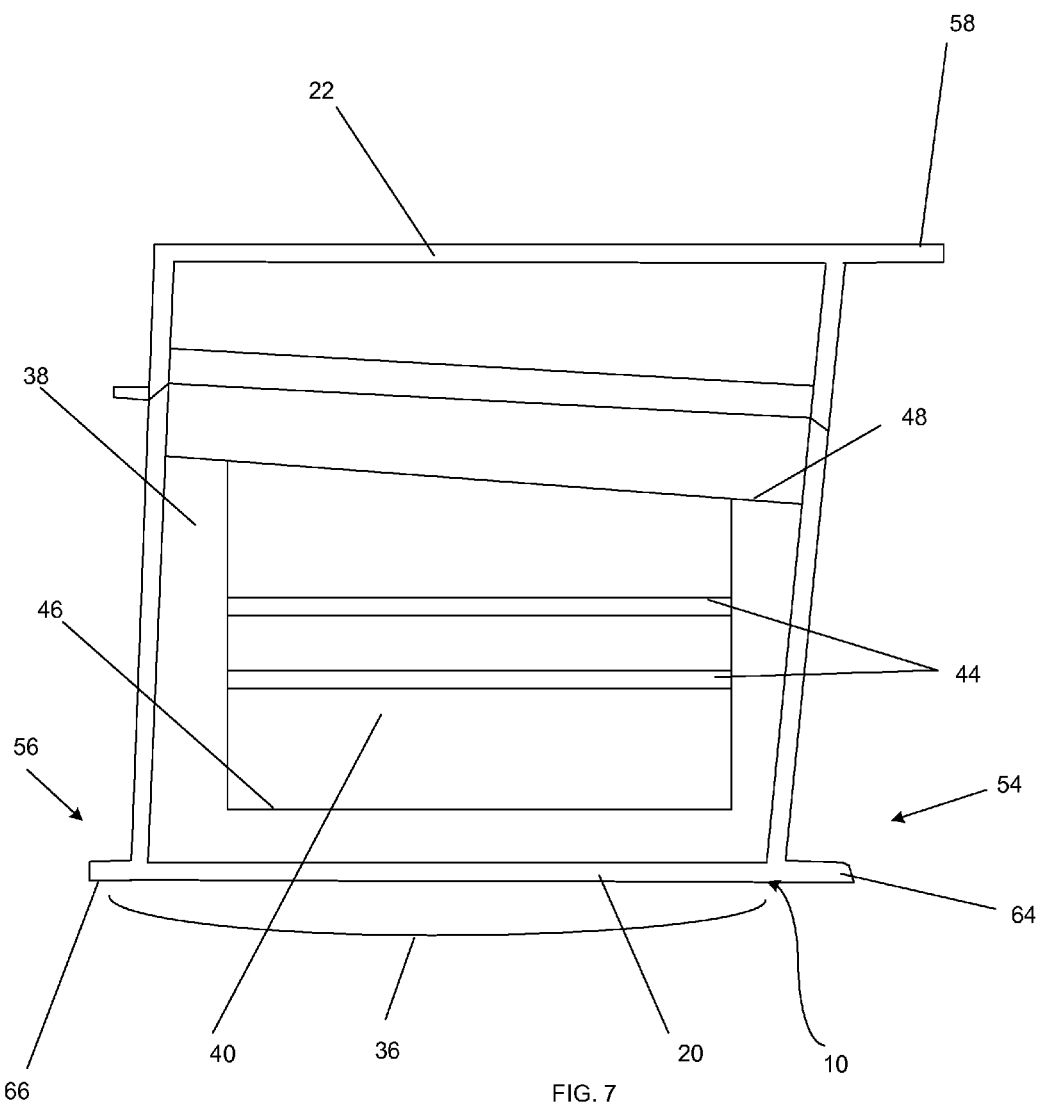
FIG. 7 shows a cross-sectional side view of a test strip container in accordance with one embodiment.

With reference to FIG. 7, another embodiment where at least one retaining member 44 is provided lengthwise along the longitudinal sides 42 (FIG. 6). In one embodiment, the retaining member 44 is located along the upper ⅓ of the longitudinal sides 42. In another embodiment, the retaining member 44 is located along the upper half of the longitudinal sides 42. In another embodiment, more than one retaining members 44 are provided along the longitudinal sides 42, for example, one retaining member 44 can be located in the top ¼ of the longitudinal sides 42, another in the top ½ of the longitudinal sides 42, and another retaining member 44 is located above the bottom ¼ of the longitudinal sides 42.

In one embodiment, the retaining member 44 comprises strips which are substantially parallel to the channel base 46. However, the strips may be oriented in a substantially parallel fashion to the insert surface 48. In yet another embodiment, the strips are angled from about 0 to about 30 degrees on the longitudinal sides 42, relative to the housing base 36. In yet another embodiment, the strips are angled from about 0 to about 15 degrees along the longitudinal sides 42.

Referring again to FIG. 1A, in one embodiment, the height H1 is less than the height H2. In one embodiment, the height H1 is about 0 to about 50 mm shorter than height H2. In yet another embodiment, the height H1 is more usually about 0 to about 20 mm shorter than the height H2. In yet another embodiment, the height H1 is most usually about 3 to about 10 mm shorter than H2.

Further referring to FIG. 1A, the difference between the heights H1 and H2 is defined by an angle α, referenced parallel to the housing base 36. In one embodiment, the angle α may range from about 0 to about 20 degrees. In another embodiment, the angle α is more usually from about 0 to about 10 degrees.

In one embodiment, the height H4 is less than the height H3. In one embodiment, the height H4 is about 0 to about 50 mm shorter than height H3. In yet another embodiment, the height H4 is about 0 to about 20 mm shorter than the height H3. In yet another embodiment, the height H4 is more usually from about 0 to about 10 mm shorter than H3.

Further referring to FIG. 1A, in one embodiment, the height difference between the heights H3 and H4 is defined by an angle β, referenced parallel to the housing base 36. In one embodiment, the angle β may range from about 0 to about 20 degrees. In another embodiment, the angle β more usually ranges from about 0 to about 10 degrees.

With reference to FIG. 1A, in one embodiment, the insert 38 further comprises an insert surface 48 sloped at an angle γ, relative to a housing base 36 (FIG. 1B). The insert surface 48 defines the top of the insert 38. Typically, the angle γ is such that the rear end of the insert surface 48 has a height greater than the front end of the insert surface 48. In one embodiment, the angle γ ranges from about 0 to about 20°. In another embodiment, the angle γ more usually ranges from about 0 to about 10°.

Referring to FIG. 4, in accordance with one embodiment, test strips 12 are placed into the channel 40, and the bottom of the test strips 12 rest on the channel base 46. The channel base 46 may be sloped to provide a platform for the test strips 12 that provides greater protrusion of the handling portion 18 above the housing distal edge 28. In one embodiment, the channel base 46 is substantially parallel to the housing base 36. In another embodiment, the channel base 46 is substantially parallel to the insert surface 48.

Figure 8:
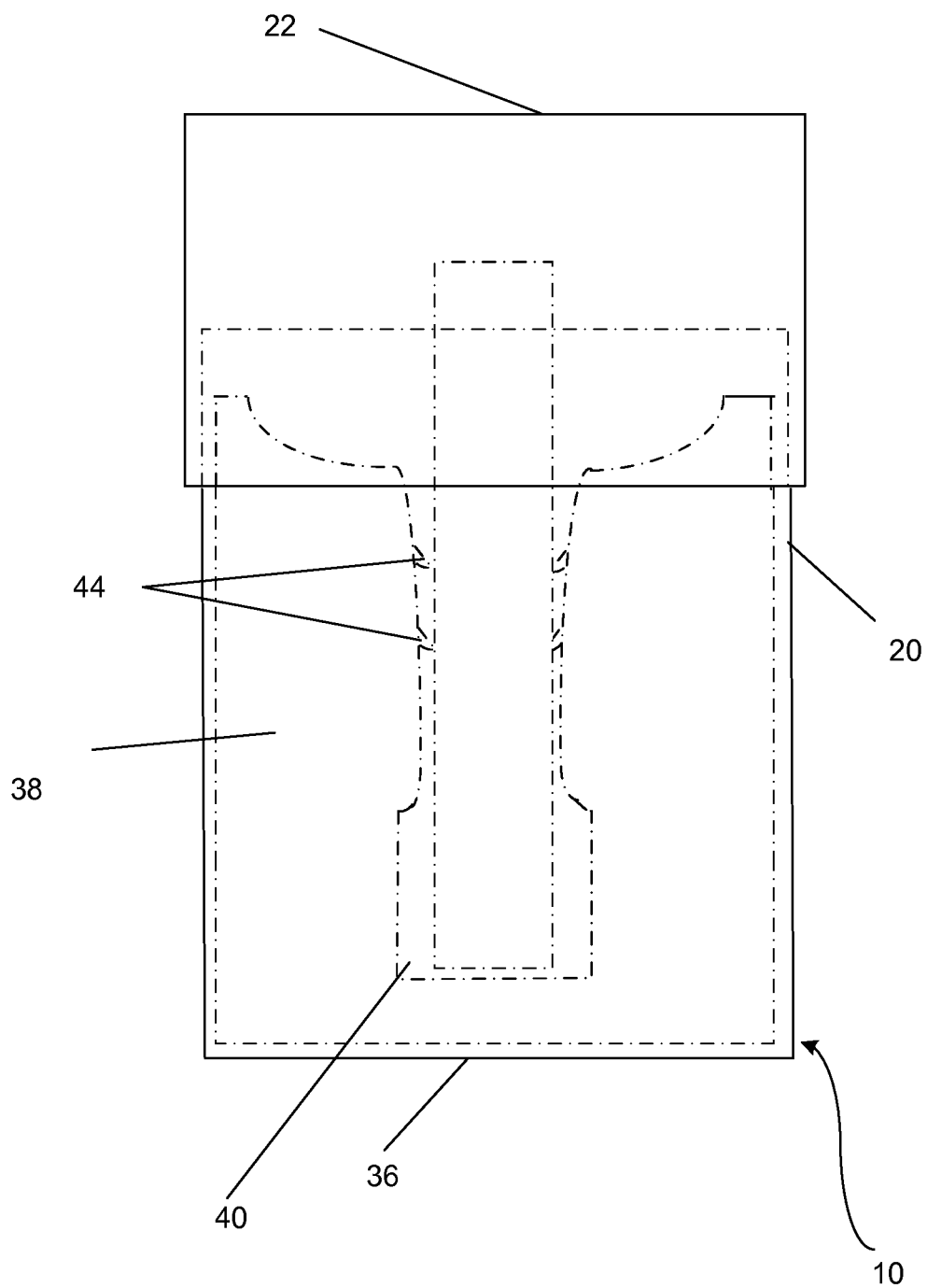
FIG. 8 shows a front cross-sectional view of a test strip container in accordance with one embodiment.

Referring to FIG. 8, in one embodiment, the retaining member 44 is an elastomeric strip co-molded into the insert 38. The retaining member 44 may also comprise more than one strip mounted along the longitudinal sides 42. The retaining member 44 may also comprise strips made up of polymers, resins, rubbers, and other flexible materials operable to releasably retain a plurality of test strips 12. In another embodiment, the retaining member 44 is mechanically attached along the longitudinal sides 42 through means commonly known by those skilled in the art.

In another embodiment, the retaining member 44 comprises an elastomer co-molded to the top of the insert 38, where a plurality of fingers extend downwards into the channel 40, and protrude inwardly towards the center of the channel 40. In one embodiment, the retaining member 44 comprises at least one finger extending into the channel 40. The retaining member 44 may also comprise fingers made up of polymers, resins, rubbers, and other flexible materials operable to releasably retain a plurality of test strips 12.

Figure 9A:
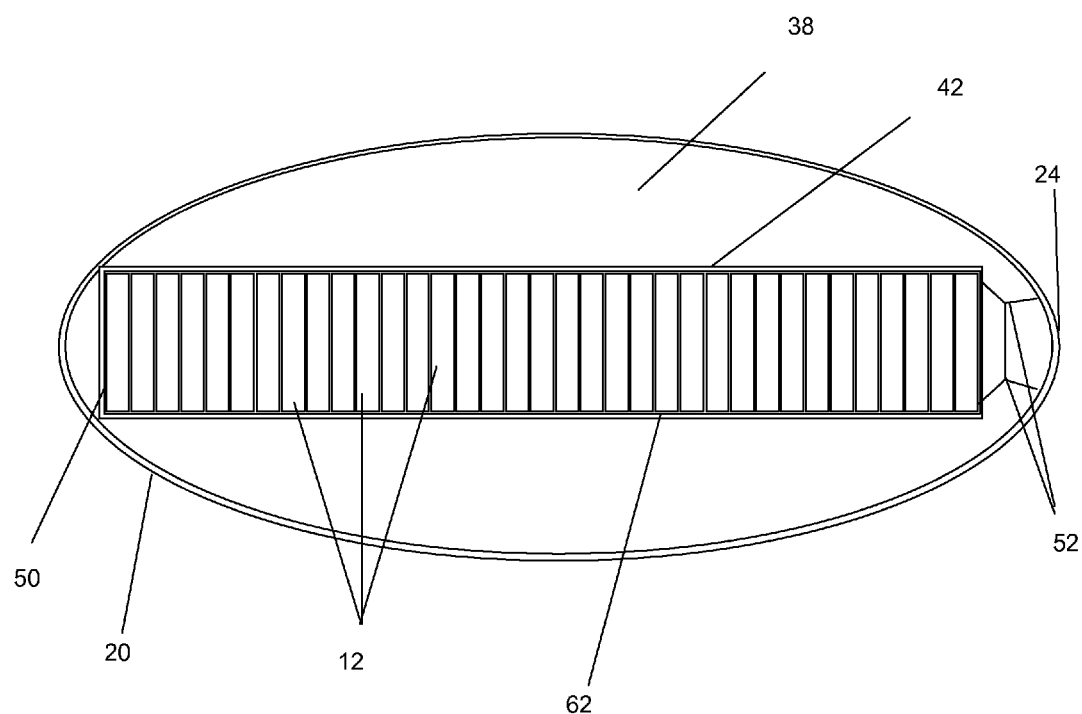
FIGS. 9A and 9B show a top view of a test strip container in accordance with one embodiment.

Referring to FIGS. 9 A and B, in one embodiment, the retaining member 44 comprises an elastic band 62 that surrounds the plurality of test strips 12 and urges the test strips 12 towards the front housing portion 24. In one embodiment, the retaining member 44 may comprise more than one elastic band. The elastic band 62 may trace the outside edges of the channel 40 to encompass a plurality of test strips 12 and urge them towards the front housing portion 24. In one embodiment, the retaining member 44 may comprise an elastic band 62 that encircles and surrounds the plurality of test strips 12. In FIG. 9A, in accordance with one embodiment, the elastic bands 62 are connected the front housing portion 24 by adhesion. In another embodiment, the elastic band 62 may be co-molded into the insert 38. In another embodiment, the elastic band 62 may be attach mechanically to the front housing portion 24.

Figure 9B:
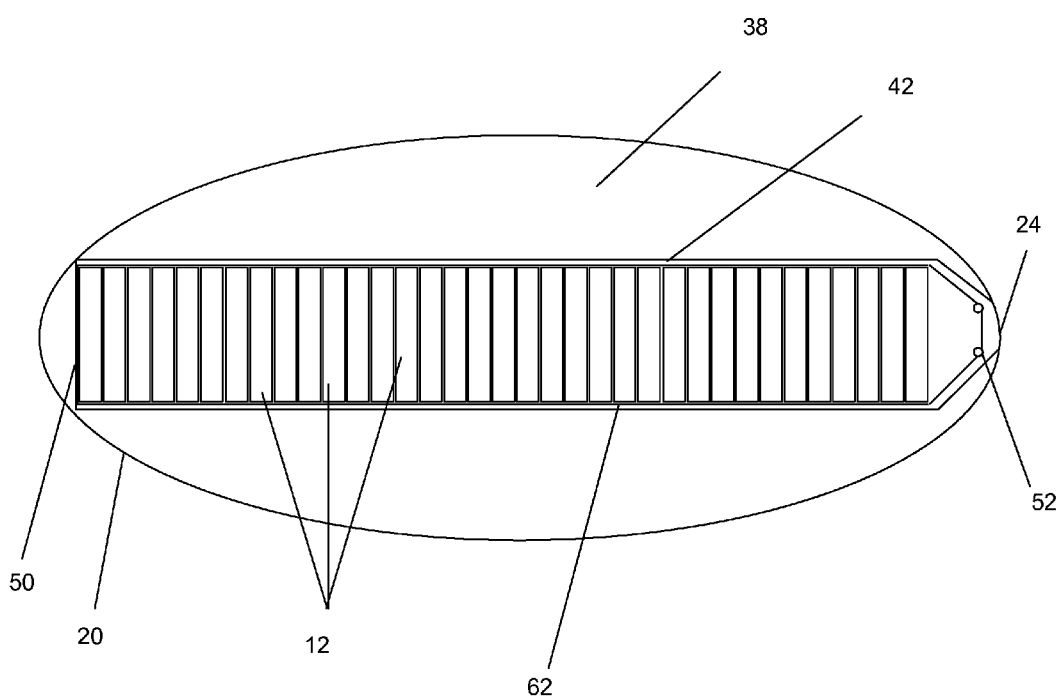

In FIG. 9B, as in accordance with another embodiment, the retaining member 44 may comprise an elastic band 62 connected to attachment posts 52 positioned adjacent to the front housing portion.

Figure 10:
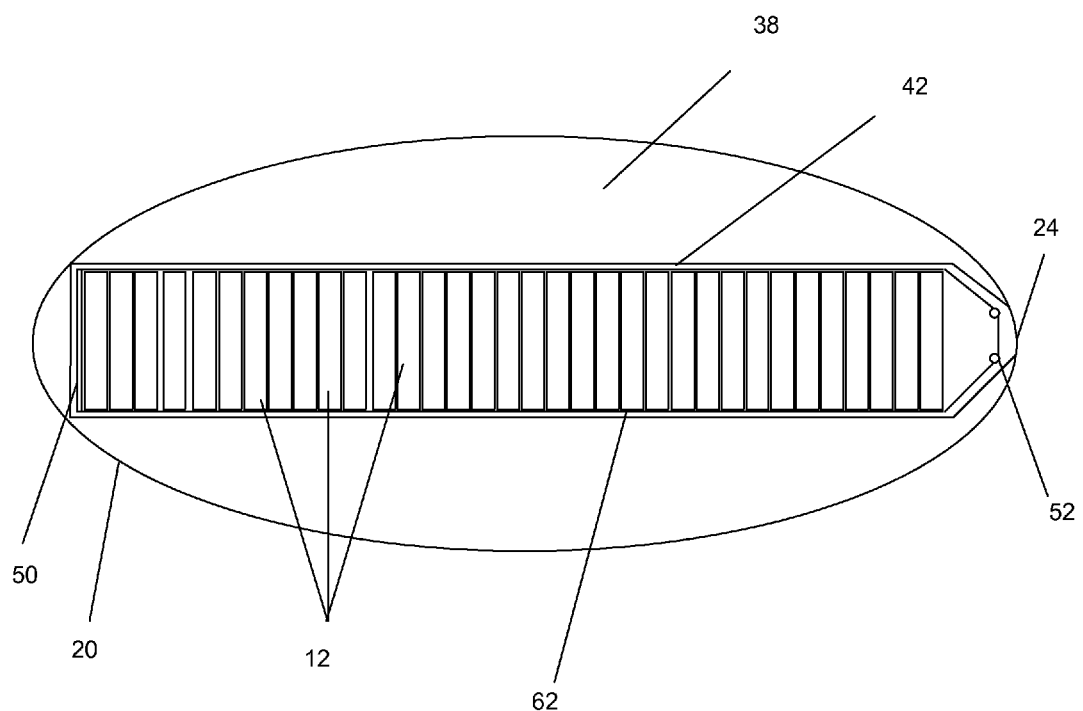
FIG. 10 shows a top view of a test strip container in accordance with one embodiment.

Referring to FIG. 10, in one embodiment, the retaining member 44 may comprise an elastic band 62 connected to an urging member 50, which presses the plurality of test strips 12 towards a front housing portion 24. The retaining member 44 may also be connected to attachment posts 52 adjacent to the front housing portion 24. The urging member 50 may comprise a wide range of material, including plastics, metals, and other suitable rigid materials. The urging member 50 may be connected to the inside of the elastic band 62 or the elastic band 62 may connect to its sides.

Figure 11:
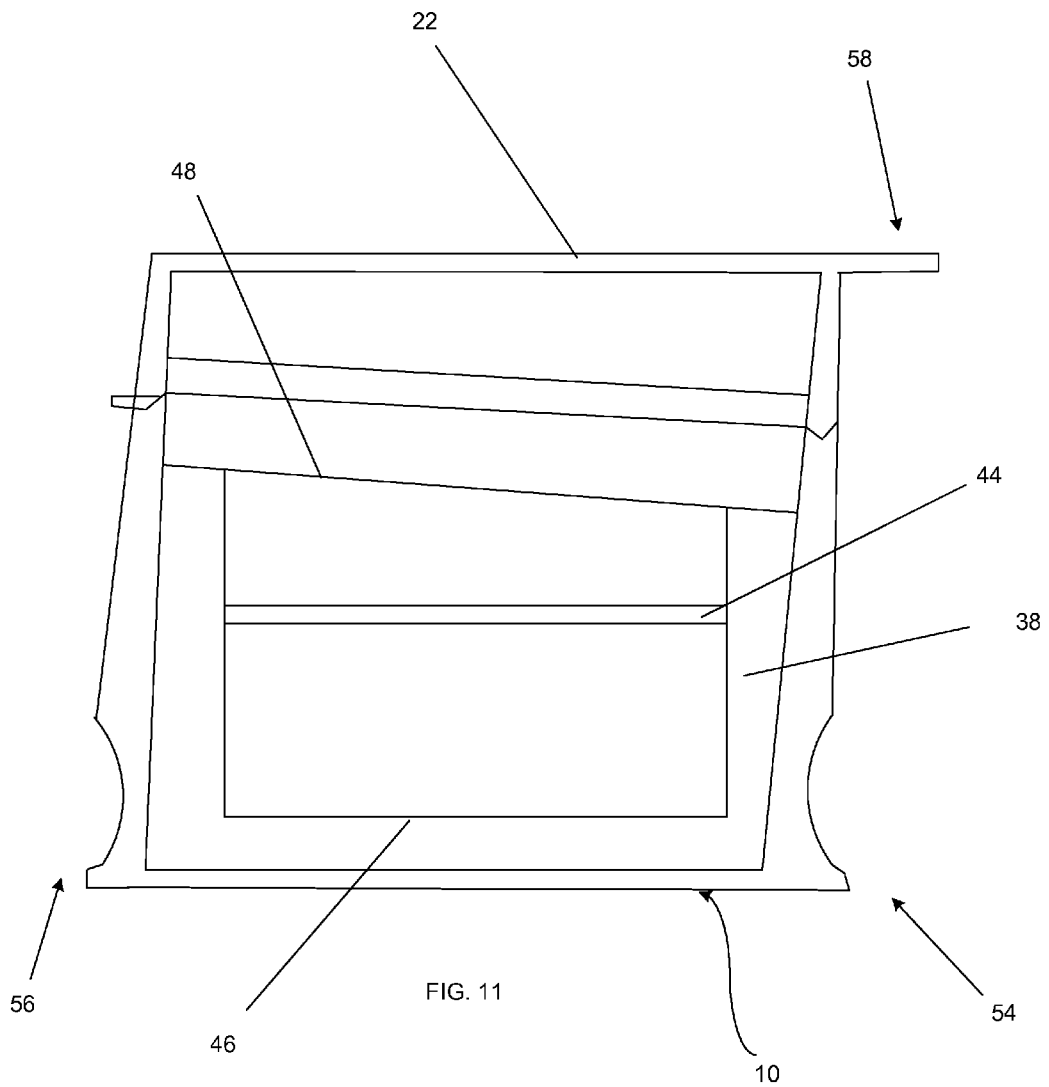
FIG. 11 shows a cross-sectional side view of a test strip container in accordance with one embodiment.

With reference to FIGS. 7 and 11, in one embodiment, the housing 20 further comprises a front grip 54 and a rear grip 56. In one embodiment, the front grip 54 comprises a tab that extends longitudinally from the bottom of the front housing portion 24 forward to allow a user to easily grasp the container 10. In another embodiment, the front grip 54 comprises an indented detent which allows a user to easily grasp the container 10 (FIG. 11). In yet another embodiment, the rear grip 56 comprises a tab that extends longitudinally from the bottom of the rear housing portion 26 backward to allow a user to easily grasp the container 10 and open the lid 22. In accordance with another embodiment, the rear grip 56 comprises an indented detent which allows a user to easily grasp the container 10.

With further reference to FIGS. 7 and 11, in accordance with one embodiment, the front grip 54 further comprises a front foot 64 that protrudes longitudinally from the front housing portion 24 (FIG. 1A). In one embodiment, the front foot 64 extends beyond the front housing portion 24 by about 3 to about 10 mm. In another embodiment, the front foot 64 extends beyond the front housing portion 24 by about 3 to about 5 mm. In accordance with another embodiment, the rear grip 56 comprises a rear foot 66 protrudes longitudinally from the rear housing portion 26 (FIG. 1A). In one embodiment, the rear foot 66 extends beyond the rear housing portion 26 by about 3 to about 10 mm. In another embodiment, the rear foot 66 extends beyond the rear housing portion 26 by about 3 to about 5 mm.

With further reference to FIG. 7, in accordance with one embodiment, the lid 22 further comprises a lid grip 58. In one embodiment, the lid grip 58 comprises a longitudinal protrusion from the front lid portion 30 to allow a user to easily open the lid 22. In another embodiment, the lid grip 58 comprises a tab extending longitudinally from the top of the front lid portion 30. In one embodiment, the lid grip 58 extends beyond the front lid portion 30 by about 3 to about 10 mm. In another embodiment, the lid grip 58 extends beyond the front lid portion 30 by about 3 to about 5 mm.

Although the description above contains many specificities, these should not be construed as limiting the scope of the embodiment but as merely providing illustrations of some of the presently preferred embodiments. For example, the container may have other shapes, such as circular, oval, trapezoidal; the compressible insert may take other forms and materials; and the test strips may be oriented in a different fashion.

Thus the scope of the various embodiments should be determined by the appended claims and their legal equivalents, rather than by the examples given.

What is claimed is:

1. A container for storing a plurality of test strips comprising:
 a housing having a front housing portion opposing a rear housing portion and a base, wherein the front housing portion has a height H1 and the rear housing portion has a height H2, wherein H1<H2, the housing defines a cavity;
 a lid hingedly connected to the rear housing portion having a front lid portion opposing a rear lid portion, wherein the front lid portion has a height H3 and the rear lid portion has a height H4, wherein H3>H4; and a removable insert provided in the cavity of the housing, wherein the removable insert includes a top surface which is sloped relative to the base of the housing, wherein the removable insert defines at least one channel therein, wherein at least one retaining member is provided lengthwise along the at least one channel, wherein each of the at least one retaining member comprises an elastomer co-molded to the removable insert, and wherein each of the at least one retaining member protrudes inwardly into the at least one channel to releasably retain the plurality of test strips substantially perpendicular to the base of the housing in the channel.

2. The container of claim 1, wherein the at least one retaining member further comprises a biasing member connected adjacent to the front housing portion which presses against and compressibly retains the plurality of test strips towards the front of the cavity.

3. The container of claim 2, wherein the biasing member comprises an elastic band which surrounds the plurality of test strips and urges the test strips towards the front housing portion.

4. The container of claim 1, wherein the height difference between heights H1 and H2 defines an angle $\alpha$ relative to horizontal, wherein the angle $\alpha >$ about 0 and $\leq$ about 14 degrees.

5. The container of claim 1, wherein the height difference between heights H3 and H4 defines an angle $\beta$ relative to horizontal, wherein the angle $\beta >$ about 0 and $\leq$ about 14 degrees.

6. The container of claim 2, wherein the top surface is angled at $\gamma$ relative to the housing base.

7. The container of claim 1, wherein the housing further comprises,
a front grip, wherein the front grip further comprises a front foot that longitudinally protrudes from the housing; and
a rear grip, wherein the rear grip comprises a rear foot that longitudinally protrudes from the housing.

8. The container of claim 1, wherein the lid further comprises,
a lip grip that comprising a longitudinal protrusion from a top of the lid.

9. The container of claim 6, wherein the angle $\gamma >$ about 0 and $\leq$ about 20 degrees.

10. The container of claim 1, wherein the at least one channel comprises a sloped channel base.

11. The container of claim 1, wherein the at least one retaining member comprises a plurality of fingers projecting downwardly into the at least one channel.

12. A container for storing a plurality of test strips comprising:
a housing defining a cavity, the housing having a base, a front grip, a rear grip, and a front housing portion, wherein the front housing portion has a height H1 opposing a rear housing portion having a height H2, wherein H1<H2 and wherein the height difference between heights H1 and H2 defines an angle $\alpha$ relative to horizontal, wherein the angle $\alpha >$ about 0 and $\leq$ about 14 degrees;
a lid hingedly connected to the rear housing portion, the lid having a front lid portion having a height H3 opposing a rear lid portion having a height H4, wherein H3>H4 and wherein the height difference between heights H3 and H4 defines an angle $\beta$ relative to horizontal, wherein the angle $\beta >$ about 0 and $\leq$ about 14 degrees; and
a removable insert provided in the cavity of the housing, wherein the removable insert has a sloped, top insert surface angled at $\gamma$ relative to the base of the housing and defines at least one channel therein, wherein at least one retaining member is provided lengthwise along said channel, and wherein each of the at least one retaining member comprises an elastomer co-molded to the removable insert, and wherein each of the at least one retaining member protrudes inwardly into the at least one channel to releasably retain the plurality of test strips substantially perpendicular to a housing base in the channel.

13. The container of claim 12, wherein the at least one retaining member further comprises a biasing member connected adjacent to the front housing portion which compressibly retains the plurality of test strips towards the front of the cavity.

14. The container of claim 12, wherein the at least one retaining member further comprises a biasing member connected adjacent to the front housing portion and connected to an urging member which compressibly retains the plurality of test strips towards the front housing portion.

15. The container of claim 12, wherein the biasing member comprises an elastic band that surrounds the plurality of test strips and urges the test strips towards the front housing portion.

* * * * *

UNITED STATES PATENT AND TRADEMARK OFFICE
CERTIFICATE OF CORRECTION

PATENT NO. : 8,844,725 B2  Page 1 of 1
APPLICATION NO. : 12/690152
DATED : September 30, 2014
INVENTOR(S) : Frank A. Chan et al.

It is certified that error appears in the above-identified patent and that said Letters Patent is hereby corrected as shown below:

In the Claims

Col. 9, Claim 8, Line 41
"a lip grip that comprising a longitudinal protrusion from a" should read
--a lip grip that comprises a longitudinal protrusion from a--.

Signed and Sealed this
Seventeenth Day of March, 2015

Michelle K. Lee
*Director of the United States Patent and Trademark Office*